(12) United States Patent
Bender et al.

(10) Patent No.: US 6,998,244 B1
(45) Date of Patent: Feb. 14, 2006

(54) CLONING AND EXPRESSION OF A NOVEL 5-HT4 RECEPTOR

(75) Inventors: Eckhard Bender, Wuppertal (DE); Armelle Nathalie Françoise Pindon, Antwerp (BE); Irma Petronella Van Oers, Zundert (NL); Mirek Jurzak, Breda (NL); Walter Herman Maria Louis Luyten, Turnhout (BE)

(73) Assignee: Janssen Pharmaceutica N.V., Beerse (BE)

( * ) Notice: Subject to any disclaimer, the term of this patent is extended or adjusted under 35 U.S.C. 154(b) by 448 days.

(21) Appl. No.: 10/018,257

(22) PCT Filed: Jun. 14, 2000

(86) PCT No.: PCT/EP00/05592

§ 371 (c)(1),
(2), (4) Date: Dec. 13, 2001

(87) PCT Pub. No.: WO00/77199

PCT Pub. Date: Dec. 21, 2000

(30) Foreign Application Priority Data

Jun. 14, 1999 (GB) .................................. 9913850

(51) Int. Cl.
*C07K 14/705* (2006.01)
*C12N 15/12* (2006.01)
*G01N 33/567* (2006.01)

(52) U.S. Cl. ................ 435/7.21; 435/69.1; 435/252.3; 435/320.1; 530/350; 536/23.5

(58) Field of Classification Search ............... 435/7.21, 435/69.1, 252.3, 320.1; 530/350; 536/23.5; 514/44
See application file for complete search history.

(56) References Cited

FOREIGN PATENT DOCUMENTS

WO WO 94/14957 A 7/1994
WO WO 00/77199 A 12/2000

OTHER PUBLICATIONS

Eckard Bender, Armelle Pindon, Irma van Oers, Yu-Bin Zhang, Walter Gommeren, Peter Verhasselt, Mirek Jurzak, Josee Leysen, and Walter Luyten, "Stucture of the Human Serotonin 5-HT(4) Receptor Gene and Cloning of a Novel 5-HT(4) Splice Variant" Journal of Neurochemistry, 2000, XP-000953119, pp. 478-483.
Olivier Blondel, Monique Gastineau, Yamina Dahmoune, Michel Langlois, and Rodolphe Fischmeister, Cloning, Expression and Pharmacology of Four Human 5-hydroxytryptamine(4) Receptor Isoforms Produced by Alternative Splicing in the Carboxyl Terminus, Journal of Neurochemistry, 1998, XP-000953121, pp. 2252-2261.
Ullmer, Christoph et al., "Expression of serotonin receptor mRNAs in blood vessels"; FEBS Letters 370 (1995) 215-221.
EP application 00 947 854.6-1223; Communication under 96(2) dated Aug. 7, 2005.

Primary Examiner—John Ulm

(57) ABSTRACT

There is disclosed an isolated or substantially pure form of a nucleic acid molecule encoding a human $5\text{-HT}_{4(h)}$ receptor, which $5\text{-HT}_{4(h)}$ receptor preferably comprises the sequence illustrated in FIG. 1B. Also provided by the invention are expression vectors incorporating said nucleic acid molecule in addition to transgenic cells, tissues or organisms transfected with the nucleic acid molecule.

14 Claims, 7 Drawing Sheets

| | | |
|---|---|---|
| h5HT4B : | VMDKLDANVSSEEGFGSVEKVVLLTFLSTVILMAILGNLLVMVAVCWDRQLRKIKTNYFIVSLAFADLLVSVLVMPF | 77 |
| h5HT4B : | GAIELVQDIWIYGEVFCLVRTSLDVLLTTASIFHLCCISLDRYYAICCQPLVYRNKMTPLRIALMIGGCWVIPTFIS | 154 |
| h5HT4B : | FLPIMQGWNNIGIIDLERSLNQGLGQDEHAIEKRKFNQNSNSTYCVFMVNKPYAITCSVVAFYIPFLLMVLAYYRIY | 231 |
| h5HT4B : | VTAKEHAHQIQMLQRAGASSESRPQSADQHSTHRMRTETKAAKTLCIIMGCFCLCWAPFFVTNIVDPFIDYTVPGQV | 308 |
| h5HT4B : | WTAFLWLGYINSGLNPFLYAFLNKSFRRAFLIILCCDDERYRRPSILGQTVPCSTTTINGSTHVLRDAVECGGQWES | 385 |
| h5HT4B : | QCHPPATSPLVAAQPSDTAPGTMQKTAMPPKEGQVLSCCL | 426 |

FIG. 1B

SEQUENCE LISTING

<160> NUMBER OF SEQ ID NOS: 13

<210> SEQ ID NO 1
<211> LENGTH: 1281
<212> TYPE: DNA
<213> ORGANISM: Homo sapiens
<220> FEATURE:
<221> NAME/KEY: CDS
<222> LOCATION: (4)..(1209)

<400> SEQUENCE: 1

```
gta atg gac aaa ctt gat gct aat gtg agt tct gag gag ggt ttc ggg       48
    Met Asp Lys Leu Asp Ala Asn Val Ser Ser Glu Glu Gly Phe Gly
    1               5                   10                  15 tca gtg gag aag gtg gtg ctg ctc acg ttt ctc tcg acg gtt atc ctg       96
Ser Val Glu Lys Val Val Leu Leu Thr Phe Leu Ser Thr Val Ile Leu
                20                  25                  30 atg gcc atc ttg ggg aac ctg ctg gtg atg gtg gct gtg tgc tgg gac      144
Met Ala Ile Leu Gly Asn Leu Leu Val Met Val Ala Val Cys Trp Asp
            35                  40                  45 agg cag ctc agg aaa ata aaa aca aat tat ttc att gta tct ctt gct      192
Arg Gln Leu Arg Lys Ile Lys Thr Asn Tyr Phe Ile Val Ser Leu Ala
        50                  55                  60 ttt gcg gat ctg ctg gtt tcg gtg ctg gtg atg ccc ttt ggt gcc att      240
Phe Ala Asp Leu Leu Val Ser Val Leu Val Met Pro Phe Gly Ala Ile
65                  70                  75 gag ctg gtt caa gac atc tgg att tat ggg gag gtg ttt tgt ctt gtt      288
Glu Leu Val Gln Asp Ile Trp Ile Tyr Gly Glu Val Phe Cys Leu Val
80                  85                  90                  95 cgg aca tct ctg gac gtc ctg ctc aca acg gca tcg att ttt cac ctg      336
Arg Thr Ser Leu Asp Val Leu Leu Thr Thr Ala Ser Ile Phe His Leu
                100                 105                 110 tgc tgc att tct ctg gat agg tat tac gcc atc tgc tgc cag cct ttg      384
Cys Cys Ile Ser Leu Asp Arg Tyr Tyr Ala Ile Cys Cys Gln Pro Leu
            115                 120                 125 gtc tat agg aac aag atg acc cct ctg cgc atc gca tta atg ctg gga      432
Val Tyr Arg Asn Lys Met Thr Pro Leu Arg Ile Ala Leu Met Leu Gly
        130                 135                 140 ggc tgc tgg gtc atc ccc acg ttt att tct ttt ctc cct ata atg caa      480
```

| | | |
|---|---|---|
| Gly Cys Trp Val Ile Pro Thr Phe Ile Ser Phe Leu Pro Ile Met Gln<br>    145                 150                 155 | | |
| ggc tgg aat aac att ggc ata att gat ttg gaa agg agt cta aac caa<br>Gly Trp Asn Asn Ile Gly Ile Ile Asp Leu Glu Arg Ser Leu Asn Gln<br>160                 165                 170                 175 | 528 | |
| ggc ctg ggc cag gat ttt cat gcg ata gaa aag agg aag ttc aac cag<br>Gly Leu Gly Gln Asp Phe His Ala Ile Glu Lys Arg Lys Phe Asn Gln<br>                180                 185                 190 | 576 | |
| aac tct aac tct acg tac tgt gtc ttc atg gtc aac aag ccc tac gcc<br>Asn Ser Asn Ser Thr Tyr Cys Val Phe Met Val Asn Lys Pro Tyr Ala<br>            195                 200                 205 | 624 | |
| atc acc tgc tct gtg gtg gcc ttc tac atc cca ttt ctc ctc atg gtg<br>Ile Thr Cys Ser Val Val Ala Phe Tyr Ile Pro Phe Leu Leu Met Val<br>        210                 215                 220 | 672 | |
| ctg gcc tat tac cgc atc tat gtc aca gct aag gag cat gcc cat cag<br>Leu Ala Tyr Tyr Arg Ile Tyr Val Thr Ala Lys Glu His Ala His Gln<br>    225                 230                 235 | 720 | |
| atc cag atg tta caa cgg gca gga gcc tcc tcc gag agc agg cct cag<br>Ile Gln Met Leu Gln Arg Ala Gly Ala Ser Ser Glu Ser Arg Pro Gln<br>240                 245                 250                 255 | 768 | |
| tcg gca gac cag cat agc act cat cgc atg agg aca gag acc aaa gca<br>Ser Ala Asp Gln His Ser Thr His Arg Met Arg Thr Glu Thr Lys Ala<br>                260                 265                 270 | 816 | |
| gcc aag acc ctg tgc atc atc atg ggt tgc ttc tgc ctc tgc tgg gca<br>Ala Lys Thr Leu Cys Ile Ile Met Gly Cys Phe Cys Leu Cys Trp Ala<br>            275                 280                 285 | 864 | |
| cca ttc ttt gtc acc aat att gtg gat cct ttc ata gac tac act gtc<br>Pro Phe Phe Val Thr Asn Ile Val Asp Pro Phe Ile Asp Tyr Thr Val<br>        290                 295                 300 | 912 | |
| cct ggg cag gtg tgg act gct ttc ctc tgg ctc ggc tat atc aat tcc<br>Pro Gly Gln Val Trp Thr Ala Phe Leu Trp Leu Gly Tyr Ile Asn Ser<br>    305                 310                 315 | 960 | |
| ggg ttg aac cct ttt ctc tac gcc ttc ttg aat aag tct ttt aga cgt<br>Gly Leu Asn Pro Phe Leu Tyr Ala Phe Leu Asn Lys Ser Phe Arg Arg<br>320                 325                 330                 335 | 1008 | |
| gcc ttc ctc atc atc ctc tgc tgt gat gat gag cgc tac cga aga cct<br>Ala Phe Leu Ile Ile Leu Cys Cys Asp Asp Glu Arg Tyr Arg Arg Pro<br>                340                 345                 350 | 1056 | |
| tcc att ctg ggc cag act gtc cct tgt tca acc aca acc att aat gga<br>Ser Ile Leu Gly Gln Thr Val Pro Cys Ser Thr Thr Thr Ile Asn Gly<br>            355                 360                 365 | 1104 | |
| tcc aca cat gta cta agg gat gca gtg gag tgt ggt ggc cag tgg gag<br>Ser Thr His Val Leu Arg Asp Ala Val Glu Cys Gly Gly Gln Trp Glu<br>        370                 375                 380 | 1152 | |
| agt cag tgt cac ccg cca gca act tct cct ttg gtg gct gct cag ccc<br>Ser Gln Cys His Pro Pro Ala Thr Ser Pro Leu Val Ala Ala Gln Pro<br>    385                 390                 395 | 1200 | |
| agt gac act taggcccctg ggacaatgac ccagaagaca gccatgcctc<br>Ser Asp Thr<br>400 | 1249 | |
| cgaaagaggg ccaggtccta agctgctgct tg | 1281 | |

<210> SEQ ID NO 2
<211> LENGTH: 402
<212> TYPE: PRT
<213> ORGANISM: Homo sapiens

<400> SEQUENCE: 2

Met Asp Lys Leu Asp Ala Asn Val Ser Ser Glu Glu Gly Phe Gly Ser
1               5                   10                  15

-continued

Val Glu Lys Val Val Leu Leu Thr Phe Leu Ser Thr Val Ile Leu Met
        20                  25                  30

Ala Ile Leu Gly Asn Leu Leu Val Met Val Ala Val Cys Trp Asp Arg
            35                  40                  45

Gln Leu Arg Lys Ile Lys Thr Asn Tyr Phe Ile Val Ser Leu Ala Phe
    50                  55                  60

Ala Asp Leu Leu Val Ser Val Leu Val Met Pro Phe Gly Ala Ile Glu
65                  70                  75                  80

Leu Val Gln Asp Ile Trp Ile Tyr Gly Glu Val Phe Cys Leu Val Arg
                85                  90                  95

Thr Ser Leu Asp Val Leu Leu Thr Thr Ala Ser Ile Phe His Leu Cys
            100                 105                 110

Cys Ile Ser Leu Asp Arg Tyr Tyr Ala Ile Cys Cys Gln Pro Leu Val
            115                 120                 125

Tyr Arg Asn Lys Met Thr Pro Leu Arg Ile Ala Leu Met Leu Gly Gly
        130                 135                 140

Cys Trp Val Ile Pro Thr Phe Ile Ser Phe Leu Pro Ile Met Gln Gly
145                 150                 155                 160

Trp Asn Asn Ile Gly Ile Ile Asp Leu Glu Arg Ser Leu Asn Gln Gly
                165                 170                 175

Leu Gly Gln Asp Phe His Ala Ile Glu Lys Arg Lys Phe Asn Gln Asn
            180                 185                 190

Ser Asn Ser Thr Tyr Cys Val Phe Met Val Asn Lys Pro Tyr Ala Ile
        195                 200                 205

Thr Cys Ser Val Val Ala Phe Tyr Ile Pro Phe Leu Leu Met Val Leu
    210                 215                 220

Ala Tyr Tyr Arg Ile Tyr Val Thr Ala Lys Glu His Ala His Gln Ile
225                 230                 235                 240

Gln Met Leu Gln Arg Ala Gly Ala Ser Ser Glu Ser Arg Pro Gln Ser
                245                 250                 255

Ala Asp Gln His Ser Thr His Arg Met Arg Thr Glu Thr Lys Ala Ala
            260                 265                 270

Lys Thr Leu Cys Ile Ile Met Gly Cys Phe Cys Leu Cys Trp Ala Pro
        275                 280                 285

Phe Phe Val Thr Asn Ile Val Asp Pro Phe Ile Asp Tyr Thr Val Pro
    290                 295                 300

Gly Gln Val Trp Thr Ala Phe Leu Trp Leu Gly Tyr Ile Asn Ser Gly
305                 310                 315                 320

Leu Asn Pro Phe Leu Tyr Ala Phe Leu Asn Lys Ser Phe Arg Arg Ala
                325                 330                 335

Phe Leu Ile Ile Leu Cys Cys Asp Asp Glu Arg Tyr Arg Arg Pro Ser
            340                 345                 350

Ile Leu Gly Gln Thr Val Pro Cys Ser Thr Thr Thr Ile Asn Gly Ser
        355                 360                 365

Thr His Val Leu Arg Asp Ala Val Glu Cys Gly Gly Gln Trp Glu Ser
    370                 375                 380

Gln Cys His Pro Pro Ala Thr Ser Pro Leu Val Ala Ala Gln Pro Ser
385                 390                 395                 400

Asp Thr

<210> SEQ ID NO 3
<211> LENGTH: 22
<212> TYPE: DNA

```
<213> ORGANISM: Artificial Sequence
<220> FEATURE:
<223> OTHER INFORMATION: PCR primer

<400> SEQUENCE: 3
cttcatggtc aacaagccct ac                                              22

<210> SEQ ID NO 4
<211> LENGTH: 28
<212> TYPE: DNA
<213> ORGANISM: Artificial Sequence
<220> FEATURE:
<223> OTHER INFORMATION: PCR primer

<400> SEQUENCE: 4
cccgttgtaa catctggatt tgvygggc                                        28

<210> SEQ ID NO 5
<211> LENGTH: 23
<212> TYPE: DNA
<213> ORGANISM: Artificial Sequence
<220> FEATURE:
<223> OTHER INFORMATION: DNA primer

<400> SEQUENCE: 5
gaaaggagtc taaaccaagg cct                                             23

<210> SEQ ID NO 6
<211> LENGTH: 30
<212> TYPE: DNA
<213> ORGANISM: Artificial Sequence
<220> FEATURE:
<223> OTHER INFORMATION: DNA primer

<400> SEQUENCE: 6
cgcatgaaaa tcctggccca ggccttggtt                                      30

<210> SEQ ID NO 7
<211> LENGTH: 21
<212> TYPE: DNA
<213> ORGANISM: Artificial Sequence
<220> FEATURE:
<223> OTHER INFORMATION: DNA primer

<400> SEQUENCE: 7
caagcagcag cttaggacct g                                               21

<210> SEQ ID NO 8
<211> LENGTH: 25
<212> TYPE: DNA
<213> ORGANISM: Artificial Sequence
<220> FEATURE:
<223> OTHER INFORMATION: DNA primer

<400> SEQUENCE: 8
ccactcatgc ttatttcctg taatg                                           25

<210> SEQ ID NO 9
<211> LENGTH: 26
<212> TYPE: DNA
<213> ORGANISM: Artificial Sequence
<220> FEATURE:
<223> OTHER INFORMATION: DNA primer

<400> SEQUENCE: 9
graayaagat gacccctctr cgyatc                                          26
```

```
<210> SEQ ID NO 10
<211> LENGTH: 26
<212> TYPE: DNA
<213> ORGANISM: Artificial Sequence
<220> FEATURE:
<223> OTHER INFORMATION: DNA primer
<220> FEATURE:
<221> NAME/KEY: misc_feature
<222> LOCATION: (6)..(6)
<223> OTHER INFORMATION: n is a, c, g, or t

<400> SEQUENCE: 10
gcccrncara tccagatgtt acaacg                                    26

<210> SEQ ID NO 11
<211> LENGTH: 31
<212> TYPE: DNA
<213> ORGANISM: Artificial Sequence
<220> FEATURE:
<223> OTHER INFORMATION: DNA primer

<400> SEQUENCE: 11
gtatgggcar yttctcsagt tcctgrtgwt g                              31

<210> SEQ ID NO 12
<211> LENGTH: 29
<212> TYPE: DNA
<213> ORGANISM: Artificial Sequence
<220> FEATURE:
<223> OTHER INFORMATION: DNA primer
<220> FEATURE:
<221> NAME/KEY: misc_feature
<222> LOCATION: (11)..(11)
<223> OTHER INFORMATION: n is a, c, g, or t

<400> SEQUENCE: 12
gaasttgctg nvrggtgrca cygactctc                                 29

<210> SEQ ID NO 13
<211> LENGTH: 30
<212> TYPE: DNA
<213> ORGANISM: Artificial Sequence
<220> FEATURE:
<223> OTHER INFORMATION: DNA primer

<400> SEQUENCE: 13
aaccaaggcc tgggccagga ttttcatggg                                30
```

CLONING AND EXPRESSION OF A NOVEL 5-HT4 RECEPTOR

CROSS-REFERENCE TO RELATED APPLICATIONS

This application claims priority from International Publication Number WO 00/77199 filed Jun. 14, 2000 and entitled "Cloning and Expression of a Novel 5-HT4 Receptor" which claims priority from Great Britain Application number 9913850.5 filed Jun. 14, 1999, the contents of which are hereby incorporated by reference.

FIELD OF THE INVENTION

The present invention is concerned with cloning and expression of a novel receptor and, in particular, with a novel nucleic acid sequence encoding a 5-$HT_4$ receptor splice variant designated herein as 5-$HT_{4(h)}$, an expression vector comprising said nucleic acid sequence, a host cell transformed or transfected with said vector, the 5-$HT_{4(h)}$ receptor protein expressed from said host cell and pharmaceutical compositions comprising said expressed protein or said nucleic acid or its complementary sequences.

BACKGROUND OF THE INVENTION

The 5-$HT_4$ receptor is widely distributed in the body, in the periphery as well as in the central nervous system. In the periphery it is found in the gastrointestinal tract, for example in the esophagus (Moummi et al., 1992), the ileum (Buchheit and Buhl, 1991) and colon (Elswood et al., 1991). It is also present in the atrium (Kaumann. et al., 1990), the bladder (Candura et al., 1996) and the adrenal glands. In the rat brain, 5-$HT_4$ mRNA has been discovered by in situ hybridization in the olfactory tubercle, the striatum and the hippocampus (Vilaro et al., 1996). The wide distribution in different tissues of the 5-$HT_4$ receptor is parallelled by a wide variety of 5-$HT_4$ variants caused by alternative splicing of exons. The splice variants described so far (Gerald et al., 1995; Claeysen et al., 1996; Van den Wyngaert et al., 1997; Claeysen et al., 1997; Blondel et al., 1997; Blondel et al., 1998) are all variations of the cytoplasmic C-terminus.

The predicted protein structures encoded by cDNA sequences already known reveal seven transmembrane domains for the complete open reading frames. In addition to their structure and 5-$HT_4$ receptor coupled signal transduction events (increase in cAMP formation, opening of K+ channels), 5-$HT_4$ receptors have also been classified as G-protein coupled receptors (GPCRs).

The present inventors have identified a novel human 5-$HT_4$ splice variant (h), which leads to the insertion of 14 amino acids into the second extracellular loop of the receptor protein. They expressed the isolated full length cDNA transiently in mammalian cells in order to compare its pharmacology with already known 5-$HT_4$ splice variants and its tissue distribution is analyzed by RT-PCR.

Therefore, according to a first aspect of the present invention, there is provided, an isolated substantially pure form of nucleic acid molecule encoding a human 5-$HT_{4(h)}$ receptor. Preferably the 5-$HT_{4(h)}$ receptor encoded by said nucleic acid molecule comprises the amino acid sequence illustrated in FIG. 1B or a functional equivalent, derivative or bioprecursor of said receptor.

Thus, the present invention comprises a nucleic acid molecule encoding a human 5-$HT_{4(h)}$ receptor or an immunologically and/or biologically active fragment thereof, which comprises a nucleotide sequence selected from the group consisting of:

(a) nucleotide sequences encoding the amino acid sequence depicted in FIG. 1B;
(b) nucleotide sequences comprising the coding sequence as depicted in FIG. 1A;
(c) nucleotide sequences encoding a polypeptide derived from the polypeptide encoded by a nucleotide sequence of (a) or (b) by way of substitution, deletion and/or addition of one or several amino acids of the amino acid sequence encoded by the nucleotide sequence of (a) or (b);
(d) nucleotide sequences the complementary strand of which hybridises with a nucleotide sequence of any one of (a) to (c);
(e) nucleotide sequences encoding a polypeptide the amino acid sequence of which has an identity of 70% or more to the amino acid sequence of the polypeptide encoded by a nucleotide sequence of any one of (a) to (d);
(f) nucleotide sequences encoding a polypeptide capable of binding a ligand of 5-$HT_{4(h)}$ comprising a fragment or an epitope-bearing portion of a polypeptide encoded by a nucleotide sequence of any one of (a) to (e);
(g) nucleotide sequences comprising at least 15 consecutive nucleotides of a nucleotide sequence of any one of (a) to (f);
(h) nucleotide sequences comprising a nucleotide sequence which is degenerated as a result of the genetic code to a nucleotide sequence of any of (a) to (g).

Advantageously, the isolated nucleic acid according to the invention may be used for expression in, for example, a host cell or the like using a suitable expression vector. Preferably, the nucleic acid may be a DNA molecule or a cDNA molecule. Preferably, the DNA molecule has the nucleic acid sequence as illustrated in FIG. 1A.

The nucleic acid molecule is preferably capable of hybridising to the sequences of the invention under conditions of high stringency or to the complement thereof.

BRIEF DESCRIPTION OF THE FIGURES

The present invention may be more clearly understood from the following exemplary embodiment with reference to the accompanying figures wherein;

FIG. 1: B) the amino acid sequences of human 5-$HT_{4(h)}$ (SEQ ID NO:2).

DETAILED DESCRIPTION OF THE INVENTION

Stringency of hybridisation as used herein refers to conditions under which polynucleic acids are stable. The stability of hybrids is reflected in the melting temperature (Tm) of the hybrids. Tm can be approximated by the formula:

$$81.5° C. + 16.6(\log_{10}[Na^+] + 0.41 (\% G\&C) - 6001/1$$

wherein 1 is the length of the hybrids in nucleotides. Tm decreases approximately by 1–1.5° C. with every 1% decrease in sequence homology.

The term "stringency" refers to the hybridisation conditions wherein a single-stranded nucleic acid joins with a complementary strand when the purine or pyrimidine bases therein pair with their corresponding base by hydrogen bonding. High stringency conditions favour homologous base pairing whereas low stringency conditions favour non-homologous base pairing.

"Low stringency" conditions comprise, for example, a temperature of about 37° C. or less, a formamide concentration of less than about 50%, and a moderate to low salt (SSC) concentration; or, alternatively, a temperature of about 50° C. or less, and a moderate to high salt (SSPE) concentration, for example 1M NaCl.

"High stringency" conditions comprise, for example, a temperature of about 42° C. or less, a formamide concentration of less than about 20%, and a low salt (SSC) concentration; or, alternatively, a temperature of about 65° C., or less, and a low salt (SSPE) concentration. For example, high stringency conditions comprise hybridization in 0.5 M NaHPO$_4$, 7% sodium dodecyl sulfate (SDS), 1 mM EDTA at 65° C. (Ausubel, F. M. et al. *Current Protocols in Molecular Biology*, Vol. I, 1989; Green Inc. New York, at 2.10.3).

"SSC" comprises a hybridization and wash solution. A stock 20× SSC solution contains 3M sodium chloride, 0.3M sodium citrate, pH 7.0.

"SSPE" comprises a hybridization and wash solution. A 1× SSPE solution contains 180 mM NaCl, 9 mM Na$_2$HPO$_4$ and 1 mM EDTA, pH 7.4.

The nucleic acid capable of hybridising to nucleic acid molecules according to the invention will generally be at least 70%, preferably at least 80 or 90% and more preferably at least 95% homologous to the nucleotide sequences according to the invention.

Advantageously, the antisense molecule may be used as a probe or as a medicament or in a pharmaceutical composition together with a pharmaceutically acceptable carrier, diluent or excipient.

The term "homologous" describes the relationship between different nucleic acid molecules or amino acid sequences wherein said sequences or molecules are related by partial identity or similarity at one or more blocks or regions within said molecules or sequences. Homology may be determined by means of computer programs known in the art.

Figure 1A:
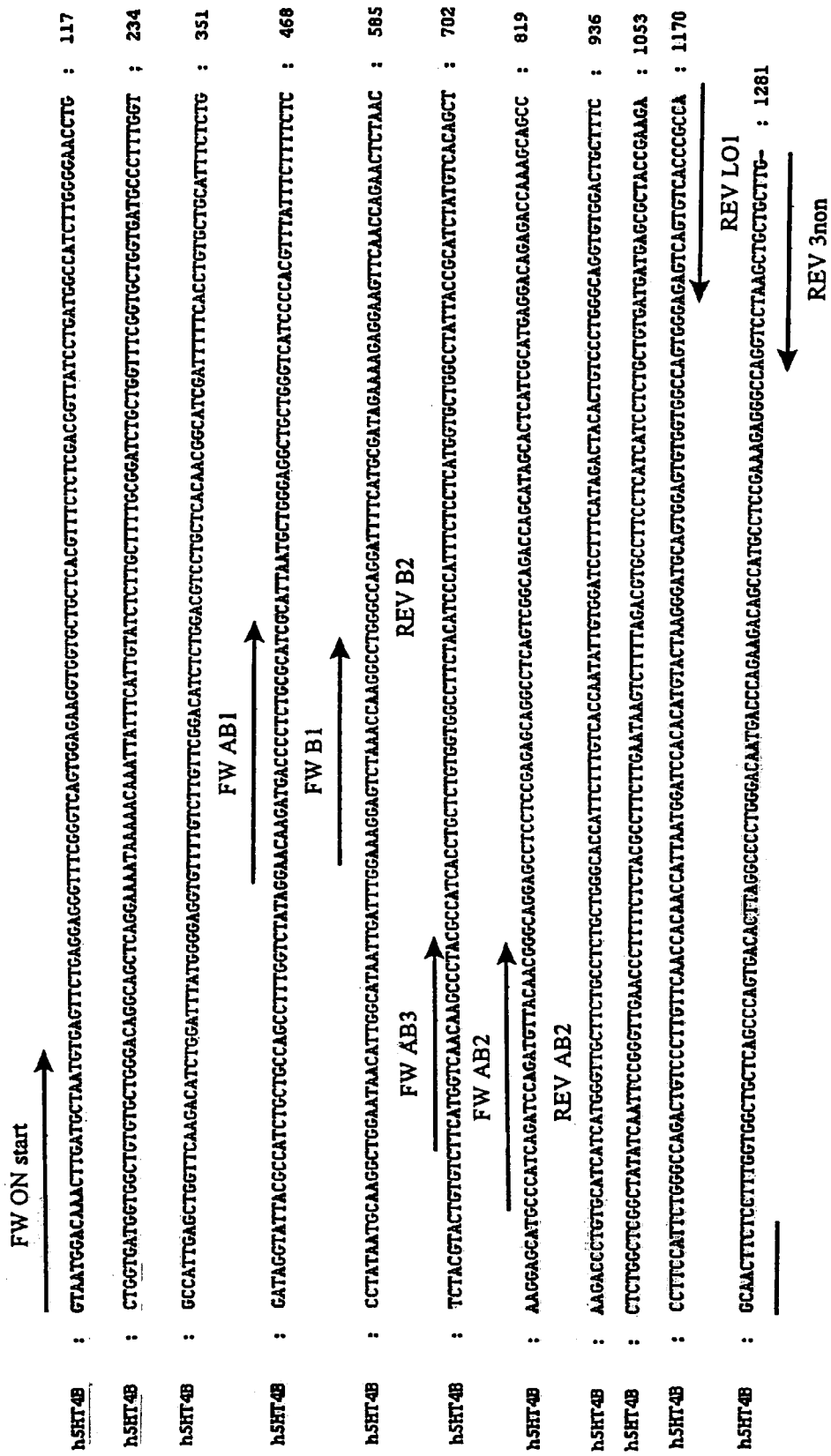
FIG. 1: A) is human 5-$HT_{4(h)}$ (SEQ ID NO:1) The positions of primers used in this study are indicated by arrows

Substantial homology preferably carries with it that the nucleotide and amino acid sequences of the 5-HT$_{4(h)}$ of the invention comprise a nucleotide and amino acid sequence fragment, respectively, corresponding and displaying a certain degree of sequence identity to the sequences in FIGS. 1A and 1B. Preferably they share an identity of at least 30%, preferably 40%, more preferably 50%, still more preferably 60%, most preferably 70%, and particularly an identity of at least 80%, preferably more than 90% and still more preferably more than 95% is desired with respect to the nucleotide or amino acid sequences depicted in FIGS. 1A and 1B, respectively. A preferred method for determining the best overall match between a query sequence (a sequence of the present invention) and a subject sequence, also referred to as a global sequence alignment, can be determined using, for example, the FASTDB computer program based on the algorithm of Brutlag et al. (Comp. App. Biosci. 6 (1990), 237–245.) In a sequence alignment the query and subject sequences are both DNA sequences. An RNA sequence can be compared by converting U's to T's. The result of said global sequence alignment is in percent identity. Further programs that can be used in order to determine homology/identity are described below and in the examples. The sequences that are homologous to the sequences described above are, for example, variations of said sequences which represent modifications having the same biological function, in particular encoding proteins with the same or substantially the same receptor specificity, e.g. binding specificity. They may be naturally occurring variations, such as sequences from other mammals, or mutations. These mutations may occur naturally or may be obtained by mutagenesis techniques. The allelic variations may be naturally occurring allelic variants as well as synthetically produced or genetically engineered variants. In a preferred embodiment the sequences are derived from a human.

According to a further aspect of the invention, there is provided a DNA expression vector comprising the DNA molecule according to the invention. This vector may advantageously be used to transform or transfect a host cell to achieve expression of the 5-HT$_{4(h)}$ receptor from said cell. Preferably, the DNA molecule is included in a plasmid such as, for example, pcDNA3 for subsequent transformation or transfection of said host cell.

An expression vector according to the invention includes a vector having a nucleic acid according to the invention operably linked to regulatory sequences, such as promoter regions, that are capable of effecting expression of said DNA fragments. The term "operably linked" refers to a juxta position wherein the components described are in a relationship permitting them to function in their intended manner. Such vectors may be transformed into a suitable host cell to provide for expression of a polypeptide according to the invention. Thus, in a further aspect, the invention provides a process for preparing polypeptides according to the invention which comprises cultivating a host cell, transformed or transfected with an expression vector as described above under conditions to provide for expression by the vector of a coding sequence encoding the polypeptides, and recovering the expressed polypeptides.

The vectors may be, for example, plasmid, virus or phage vectors provided with an origin of replication, optionally a promoter for the expression of said nucleotide and optionally a regulator of the promoter. The vectors may include a coding sequence fused in frame to a marker sequence which allows for purification of the polypeptide of the invention. In addition the vector may contain a sequence coding a phenotypic trait for selection of transformed cells such as, for example, ampicillin resistance.

Regulatory elements required for expression include promoter sequences to bind RNA polymerase and transcription initiation sequences for ribosome binding. For example, a bacterial expression vector may include a promoter such as the lac promoter and for transcription initiation in the Shine-Dalgarno sequence and the start codon AUG. Similarly, a eukaryotic expression vector may include a heterologous or homologous promoter for RNA polymerase II, a downstream polyadenylation signal, the start codon AUG, and a termination codon for detachment of the ribosome. Such vectors may be obtained commercially or assembled from the sequences described by methods well known in the art.

Transcription of DNA encoding the polypeptides of the present invention by higher eukaryotes is optimised by including an enhancer sequence in the vector. Enhancers are cis-acting elements of DNA that act on a promoter to increase the level of transcription. Vectors will also generally include origins of replication in addition to the selectable markers.

Nucleic acid molecules according to the invention may be inserted into the vectors described in an antisense orientation in order to provide for the production of antisense RNA. Antisense RNA or other antisense nucleic acids may be produced by synthetic means.

In accordance with the present invention, a defined nucleic acid includes not only the identical nucleic acid but also any amino base variations including, in particular, substitutions in bases which result in a synonymous codon (a different codon specifying the same amino acid residue) due to the degenerate code in conservative amino acid substitutions. The term "nucleic acid sequence" also includes the complementary sequence to any single stranded sequence given regarding base variations.

The present invention also advantageously provides nucleic acid sequences of at least approximately 10 contiguous nucleotides of a nucleic acid according to the invention and preferably from 10 to 50 nucleotides. These sequences may, advantageously, be used as probes or primers to initiate replication, or the like. Such nucleic acid sequences may be produced according to techniques well known in the art, such as, by recombinant or synthetic means. They may also be used in diagnostic kits or the like for detecting the presence of a nucleic acid according to the invention. These tests generally comprise contacting the probe with the sample under hybridising conditions and detecting for the presence of any duplex or triplex formation between the probe and any nucleic acid in the sample.

According to the present invention these probes may be anchored to a solid support. Preferably, they are present on an array so that multiple probes can simultaneously hybridize to a single biological sample. The probes can be spotted onto the array or synthesised in situ on the array. (See Lockhart et al., Nature Biotechnology, vol. 14, December 1996 "Expression monitoring by hybridisation into high density oligonucleotide arrays". A single array can contain more than 100, 500 or even 1,000 different probes in discrete locations.

The nucleic acid sequences, according to the invention may be produced using such recombinant or synthetic means, such as, for example, using PCR cloning mechanisms which generally involve making a pair of primers, which may be from approximately 10 to 50 nucleotides to a region of the gene which is desired to be cloned, bringing the primers into contact with mRNA, cDNA, or genomic DNA from a human cell, performing a polymerase chain reaction under conditions which bring about amplification of the desired region, isolating the amplified region or fragment and recovering the amplified DNA. Generally, such techniques as defined herein are well known in the art, such as described in Sambrook et al (Molecular Cloning: a Laboratory Manual, 1989).

The nucleic acids or oligonucleotides according to the invention may carry a revealing label. Suitable labels include radioisotopes such as $^{32}P$ or $^{35}S$, enzyme labels or other protein labels such as biotin or fluorescent markers. Such labels may be added to the nucleic acids or oligonucleotides of the invention and may be detected using known techniques per se.

Advantageously, human allelic variants or polymorphisms of the DNA molecule according to the invention may be identified by, for example, probing cDNA or genomic libraries from a range of individuals, for example, from different populations. Furthermore, nucleic acids and probes according to the invention may be used to sequence genomic DNA from patients using techniques well known in the art, such as the Sanger Dideoxy chain termination method, which may, advantageously, ascertain any predisposition of a patient to certain disorders associated with a growth factor according to the invention.

The present invention also comprises within its scope proteins or polypeptides encoded by the nucleic acid molecules according to the invention or a functional equivalent, derivative or bioprecursor thereof. Preferably, the protein comprises the amino acid sequence illustrated in FIG. 1B.

A "functional equivalent" as defined herein should be taken to mean a receptor that exhibits the same properties and functionality associated with the $5HT_{4(h)}$ receptor according to the invention. A "derivative" should be taken to mean a polypeptide or protein in which certain amino acids may have been altered or deleted or replaced and which polypeptide or protein retains biological activity of said $5HT_{4(h)}$ receptor and/or which can cross react with antibodies raised using a receptor according to the invention as the challenging antigen.

Encompassed with the scope of the invention are hybrid and modified forms of the $5HT_{4(h)}$ receptor according to the invention including fusion proteins and fragments. The hybrid and modified forms include, for example, when certain amino acids have been subjected to some modification or replacement, such as for example, by point mutation and yet which results in a protein which possesses the same receptor specificity as the $5HT_{4(h)}$ of the invention.

The protein according to the invention should be taken to include all possible amino acid variants encoded by the nucleic acid molecule according to the invention including a polypeptide encoded by said molecule and having conservative amino acid changes. Proteins or polypeptides according to the invention further include variants of such sequences, including naturally occurring allelic variants which are substantially homologous to said proteins or polypeptides. In this context, substantial homology is regarded as a sequence which has at least 70%, and preferably 80 or 90% amino acid homology with the proteins or polypeptides encoded by the nucleic acid molecules according to the invention.

As is well known in the art many proteins are produced in vivo with a (pre) signal at the N terminus of the protein and which may be required for transport of the protein across the cell membrane. Furthermore, such proteins may comprise a further pro sequence that represents a stable precursor to the mature protein. Such pre and pro sequences are not required for biological activity. Furthermore, in eukaryotic organisms many proteins are subjected to glycosylation so as to confer biological activity in vivo. References to a bioprecursor, in accordance with the present invention, refers to all such forms of the protein or polypeptide of the invention prior to any such post translational modification.

A further aspect of the invention comprises the host cell itself transformed with the DNA expression vector described herein, which host cell preferably comprises a eukaryotic cell, which may be for example, a mammalian cell, an insect cell or yeast cell or the like. In one embodiment the cell comprises a human embryonic kidney cell and preferably a cell of the HEK293 cell line. Alternatively, the cell may comprise NIH/3T3 mouse fibroblasts or Chinese hamster ovary (CHO) cells or COS-7 cells.

Further provided by the present invention is a transgenic cell, tissue or organism comprising a transgene capable of expressing a human $5\text{-}HT_{4(h)}$ receptor according to the invention, or expressing a functional equivalent, fragment, derivative or bioprecursor of said receptor. The term "transgene capable of expression" as used herein means a suitable nucleic acid sequence which leads to the expression of a human $5\text{-}HT_{4(h)}$ receptor having the same function and/or activity. The transgene may include, for example, genomic nucleic acid isolated from human cells or synthetic nucleic acid including cDNA integrated into the genome or in an extra chromosomal state. Preferably, the transgene comprises the nucleic acid sequence encoding the $5\text{-}HT_{4(h)}$ receptor as described above, or a functional fragment of said nucleic acid. A functional fragment of said nucleic acid should be taken to mean a fragment of the gene comprising said nucleic acid, coding for the $5\text{-}HT_{4(h)}$ receptor or a functional equivalent, derivative or bioprecursor of said receptor. For example, the gene may comprise deletions or mutations but may still encode a functional $5\text{-}HT_{4(h)}$ receptor protein.

There is also provided by a further aspect of the present invention, a purified human $5\text{-}HT_{4(h)}$ receptor expressed by a host cell or a transgenic cell tissue or organism according to the invention. Also provided by the invention are membrane preparations from cells expressing a human $5\text{-}HT_{4(h)}$ receptor.

The nucleic acid or protein according to the invention may be used as a medicament or in the preparation of a medicament for treating cancer or other diseases or conditions associated with expression of $5\text{-}HT_{4(h)}$ receptor protein.

Advantageously, the nucleic acid molecule or the protein according to the invention may be provided in a pharmaceutical composition together with a pharmacologically acceptable carrier, diluent or excipient therefor.

The present invention is further directed to inhibiting $5\text{-}HT_{4(h)}$ in vivo by the use of antisense technology. Antisense technology can be used to control gene expression through triple-helix formation or antisense DNA or RNA, both of which methods are based on binding of a polynucleotide to DNA or RNA. For example, the 5' coding portion of the mature protein sequence, which encodes for the protein of the present invention, is used to design an antisense RNA oligonucleotide of from 10 to 40 base pairs in length. A DNA oligonucleotide is designed to be complementary to a region of the gene involved in transcription (triple-helix—see Lee et al. Nucl. Acids Res., 6:3073 (1979); Cooney et al., Science, 241:456 (1988); and Dervan et al., Science, 251:1360 (1991), thereby preventing transcription and the production of $5\text{-}HT_{4(h)}$ The antisense RNA oligonucleotide hybridises to the mRNA in vivo and blocks translation of an mRNA molecule into the $5\text{-}HT_{4(h)}$ receptor.

Alternatively, the oligonucleotide described above can be delivered to cells by procedures in the art such that the anti-sense RNA and DNA may be expressed in vivo to inhibit production of a polypeptide of the invention in the manner described above.

Antisense constructs to the nucleotide sequence encoding $5\text{-}HT_{4(h)}$, therefore, may inhibit the expression of the $5\text{-}HT_{4(h)}$ receptor and may therefore be used to treat conditions associated with expression or overexpression of $5\text{-}HT_{4(h)}$ according to the invention.

A further aspect of the invention comprises the host cell itself transformed with the DNA expression vector described herein, which host cell preferably comprises a mammalian cell such as, for example, a COS-7 cell or a human cell such as a human embryonic kidney (HEK) 293 cell or the like.

Incorporation of cloned DNA into a suitable expression vector for subsequent transformation of the cell and subsequent selection of the transformed cells is well known to those skilled in the art as provided in Sambrook et al., (1989) "Molecular Cloning, A Laboratory Manual, Cold Spring Harbour Laboratory Press".

Antibodies to the human $5\text{-}HT_{4(h)}$ receptor are also provided which may be used in a medicament or in a pharmaceutical composition.

Antibodies to the protein or polypeptide of the present invention may, advantageously, be prepared by techniques which are known in the art. For example, polyclonal antibodies may be prepared by inoculating a host animal, such as a mouse, with the polypeptide according to the invention or an epitope thereof and recovering immune serum. Monoclonal antibodies may be prepared according to known techniques such as described by Kohler R. and Milstein C., Nature (1975) 256, 495–497.

Antibodies according to the invention may also be used in a method of detecting for the presence of a receptor according to the invention, which method comprises reacting the antibody with a sample and identifying any protein bound to said antibody. A kit may also be provided for performing said method which comprises an antibody according to the invention and means for reacting the antibody with said sample.

Advantageously, the antibody according to the invention may also be used as a medicament or in the preparation of a medicament for treating diseases associated with expression of $5\text{-}HT_{4(h)}$. The invention also further provides a pharmaceutical composition comprising said antibody together with a pharmaceutically acceptable carrier, diluent or excipient therefor.

Proteins which interact with the polypeptide of the invention may be identified by investigating protein—protein interactions using the two-hybrid vector system first proposed by Chien et al (1991), Proc. Natl. Acad. Sci. USA 88: 9578–9582.

This technique is based on functional reconstitution in vivo of a transcription factor which activates a reporter gene. More particularly the technique comprises providing an appropriate host cell with a DNA construct comprising a reporter gene under the control of a promoter regulated by a transcription factor having a DNA binding domain and an activating domain, expressing in the host cell a first hybrid DNA sequence encoding a first fusion of a fragment or all of a nucleic acid sequence according to the invention and either said DNA binding domain or said activating domain of the transcription factor, expressing in the host at least one second hybrid DNA sequence, such as, a library or the like, encoding putative binding proteins to be investigated together with the DNA binding or activating domain of the transcription factor which is not incorporated in the first fusion; detecting any binding of the proteins to be investigated with a protein according to the invention by detecting for the presence of any reporter gene product in the host cell; optionally isolating second hybrid DNA sequences encoding the binding protein.

Proteins which bind to the 5-HT$_{4(h)}$ receptor can be identified using this technique. The proteins identified can also be used to identify compounds which acts as agonists/antagonists of these proteins. The structure of the receptor can also be used to design agonists or antagonists of the receptor. The present invention also comprises an agonist or antagonist of the human 5-HT$_{4(h)}$ receptor according to the invention which agonist or antagonist advantageously may also be used as a medicament or in a pharmaceutical composition together with a pharmaceutically acceptable carrier diluent or excipient therefor.

The present invention is also directed to antagonists and inhibitors of the 5-HT$_{4(h)}$ receptor of the present invention. The antagonists and inhibitors are those substances which inhibit or eliminate the function of such a receptor. The present invention further relates to agonists and stimulators of a receptor of the present invention. The agonists and stimulators are those substances which enhance the function or activity or the expression of such a receptor.

Further provided by the present invention is a method of determining whether a compound is an agonist or an antagonist of a 5-HT$_{4(h)}$ receptor protein, which method comprises contacting a host cell or transgenic cell tissue or organism according to the invention expressing said 5-HT$_{4(h)}$ receptor protein with said compound in the presence of a protein which binds to said receptor and monitoring induced cAMP formation in said cell. Preferably, the cell is a mammalian cell such as a COS-7 cell or the like or a human cell, such as a human embryonic kidney (HEK) 293 cell or the like. A further method of determining whether a compound is an agonist or an antagonist of 5-HT$_{4(h)}$ ligand protein is provided which method comprises contacting a cell or membrane preparation of said host cell or said transgenic cell according to the invention with said compound and establishing the binding affinity of said compound for said receptor. Any compounds identified may advantageously be used as a medicament or in a pharmaceutical composition together with an appropriate diluent or excipient.

Antagonists of the 5-HT$_{4(h)}$ receptor according to the invention may be useful in treating any of heartburn, reflux, esophagitis, Barrett's esophagus, esophageal cancer, achalasia, esophageal stenosis, esophagel spasms, esophageal hiatal hernia or other esophageal motility disorders, oesophageal irritation, such as asthma, bronchospasms, aspiration and its consequences (bronchitis, (broncho)pneumonia, bronchiectasia) and other diseases of the lower oesophageal sphincter, or achalasia; oesophageal stenosis (due to systemic sclerosis, tumours, burns, or the like) or compression, oesophageal spasms or other oesophageal motility disorders, asthma, irritable bowel syndrome, bronchospasms and other airway disorders possibly connected with oesophageal irritation aspiration and its consequence (bronchitis, (broncho) pneumonia, bronchiectasia); (hiatus) hernia; denervation of the oesophagus (e.g. after certain types of trauma or surgery), disturbances in oesophageal innervation.

Further provided by the present invention is a diagnostic kit for determining whether a compound is an agonist or an antagonist in relation to 5-HT$_{4(h)}$ receptor ligand or an antibody thereto. The kit may comprise a cell according to the invention, means for contacting said compound with said cell and means for measuring cAMP formation in said cell. Alternatively, the kit may comprise a probe, including any of a nucleic acid molecule encoding a 5-HT$_{4(h)}$ receptor according to the invention, a molecule capable of hybridising thereto under high stringency conditions, a fragment of said nucleic acids, an antisense molecule according to the invention, together with means for contacting biological material to be tested with said probe.

Disorders mediated by activation or expression of the 5-HT$_{4(h)}$ receptor may, advantageously, be treated by administering to an individual an amount of a compound identified as an agonist of the ligand binding 5HT$_{4(h)}$ in sufficient concentration to reduce or prevent the symptoms of the disorder.

Materials and Methods

Materials

AmpliTaq Gold, dNTPs, MgCl$_2$, and PCR bufferII were obtained from Perkin-Elmer Cetus (Foster City, Calif., U.S.A.). T4 DNA ligase and restriction endonucleases were products of Boehringer (Mannheim, Germany). The Multiprime DNA labeling system and [$^3$H]GR 113808 with a specific activity of 3.07 TBq/mmol were obtained from Amersham (Little Chalfort, U.K.). The ExpressHybTM hybridization solution and the Smart cDNA synthesis kit were from Clontech (Palo Alto, Calif., U.S.A.). [$^{32}$P] dCTP was purchased from NEN DuPont (Wilmington, Del., U.S.A.). Plasmid preparation kits and the Qiaquick PCR amplification kit were from Qiagen (Hilden, Germany). The PRISM Ready Reaction Dye Terminator Cycle Sequencing kits and the ABI 377 or 373A sequencing machines were from Applied Biosystems (Foster City, Calif., U.S.A.). The Geneamp PCR System 9600 was from Perkin-Elmer (Norwalk, Conn., U.S.A.). The mammalian expression vector pcDNA3 was obtained from Invitrogen (Carlsbad, Calif., U.S.A.). Dulbecco's modified Eagle medium (DMEM) and foetal calf serum were from Life Technologies (Gaithersburg, Md., U.S.A.). The Bradford protein assay was performed with the reagent supplied from Bio-Rad (Nazareth Eke, Belgium), which also supplied the Zeta-Probe blotting membrane. The NEN flash plate assay was supplied by DuPont de Nemours (Brussels, Belgium). The liquid scintillation spectrometer and the scintillation fluid Ultima Gold MV were from Packard (Meriden, Conn., U.S.A.). All compounds were dissolved and diluted in dimethyl sulfoxide (DMSO; except the indoleamines, which were dissolved in water and protected from light throughout the experiment). The final DMSO concentration in the test did not exceed 0.5% (vol/vol). The GraphPad Prism program was from GraphPad Software, Inc. (San Diego, Calif., U.S.A.).

General Molecular Biological Methods

Unless otherwise indicated, all PCR reactions were performed in a total volume of 50 µl, containing 1 µl of cDNA and 1.25 U of AmpliTaq Gold in 1×PCR buffer II, 200 mM dNTPs, 400 nM primers, and 2.0 mM $MgCl_2$. PCR conditions were 10 min of denaturation at 95° C., followed by 35 cycles of 10 seconds at 95° C., 30 seconds at 53° C., and 2 min at 72° C., followed by a 10 min incubation at 72° C. DNA manipulations were done according to standard protocols (Maniatis et al., 1982). DNA sequencing was carried out with reagents from the PRISM Ready Reaction Dye Terminator Kit and run on a GeneAmp PCR System 9600 according to the specifications of the supplier.

BAC Library Screening

A human genomic DNA library in pBeloBAC11, Research Genetics (Huntsville, Ala., U.S.A.) was screened by PCR using two primers, FW AB3 5'CTTCATGGTCAA-CAGCCCCTAC 3' (SEQ ID NO:3) and REV AB2 5'CCCGTTGTAACATCTGGATTTGVYGGGC3'(SEQ ID NO:4), specific for the 5-$HT_4$ cDNA. The position of the primers on the cDNA sequence is indicated in FIG. 1. The PCRs were set up as described above in a total volume of 30 µl, 1 µl of the BAC pools supplied by Research Genetics was used as substrate. BAC DNA was prepared using the Qiagen Maxi preparation kit (Hilden, Germany).

PCR Amplification of the 5' and 3' ends of the Human 5-$HT_{4(h)}$ and Assembly to a Full Length Coding Region Based on the nucleotide sequence of the 5-$HT_{4(h)}$ specific exon, derived from BAC clone 228K23 (Research Genetics), 2 primers were designed. Forward primer FW B1 (5'GAAAGGAGTCTAAACCAAGGCCT3', SEQ ID NO:5) and reverse primer REV B2 (5'CGCATGAAAA TCCTG-GCCCAGGCCTTGGTT3', SEQ ID NO:6) hybridizing at positions indicated in FIG. 1A. Primer FW B1 was combined with reverse primer REV 3non (5'CAAGCAG-CAGCTTAGGACCTG3', SEQ ID NO:7) and reverse primer REV B2 was combined with forward primer FW ONstart (5'CCACTC ATGCTTATTTCCTGTAATG3', SEQ ID NO:8). PCR reactions were set up on cDNA prepared from human lower esophageal sphincter using Advantage Taq and initial denaturation for 1 min at 95° C. The resulting PCR products were cloned into EcoRV cut and dephosphorylated pcDNA3 (Invitrogen, Carlsbad, Calif., U.S.A.). PCR products representing 5' and 3' part of the 5-$HT_{4(h)}$ were blunted by Klenow treatment and subsequently digested with the restriction enzyme StyI before ligation into pcDNA3.

mRNA Tissue Distribution Analysis

Total RNA from the different tissues analysed was prepared by the CsCl method, cDNA was prepared thereof using the Smart cDNA library kit from Clontech (Palo Alto, Calif., U.S.A.), 0.5 ml of the reaction product was used per PCR. The tissue distribution experiments were done by PCRs, using 3 different forward primers and 4 different reverse primers. One forward primer, FW B1 is specific for cDNAs containing the 5-$HT_{4(h)}$ exon, the two others FW AB1 (5'GRAAYAAGATGACCCCTCTRCGYATC3', SEQ ID ON:9) and FW AB2 (5'GCCCRNCARATCCAGATGT-TACAACG3', (SEQ ID NO:10) will amplify all 5-$HT_4$ messages. Among the four reverse primers, one REV AB2 will amplify all 5-$HT_4$ messages, the other three reverse primers are specific for 5-$HT_{4(a)}$ (REV SH1, 5'GTATGGGCARYTTCTCS AGT TCCTGRTGWTG3', SEQ ID NO:11), 5-$HT_{4(b)}$(REV LO1, 5'GAASTGCTGNVRGGTGRCA-CYGACTCTC3', SEQ ID NO:12) AND 5-$HT_{4(h)}$ (REV B2). The position of the primers is indicated in FIG. 1. The PCR reactions were separated on an agarose gel and blotted on Zeta-Probe blotting membrane. A $^{32}P$-labeled probe (Multiprobe DNA labeling system (Amersham)) corresponding to the human 5-$HT_{4(b)}$ cDNA (Van den Wyngaert et al., 1997) was hybridized to the PCR products on the membrane according to the instructions of the ExpressHybTM user manual (Clontech, Palo Alto, Calif., U.S.A.).

Expression of the Human 5-$HT_{4(h)}$ Receptor in Mammalian Cells and Pharmacological Characterization COS-7 cells were grown in DMEM supplemented with 10% fetal calf serum. A large scale plasmid preparation of 5-$HT_{4(h)}$/pcDNA3 was made using the Qiagen large scale plasmid preparation kit. Plasmid DNA was transfected into COS-7 cells as described in Van den Wyngaert et al. (1997). 48 hours after transfection the cells were harvested and used for membrane preparation or cyclic AMP formation assays as described (Van den Wyngaert et al., 1997).

Membrane Preparation

The transfected COS-7 cells were cultured on 150 mm Petri dishes and washed twice with ice-cold phosphate-buffered saline. The cells were then scrapped from the plates with a cell scraper, suspended in 50 mM Tris-HCl buffer, pH 7.4, and harvested by centrifugation for 10 min at 16000 g. The pellet was resuspended in 5 mM Tris-HCl, pH 7.4, and homogenized with an Ultra Turax homogenizer; the resulting membranes were collected by centrifugation for 20 min at 25000 g. Membranes were stored at −70° C. in 50 mM Tris-HCl buffer, pH 7.4, at a protein concentration of 1 mg/ml. The Bradford protein assay was used for protein determination with bovine serum albumin as a standard.

Radioligand Binding

Assay mixtures (0.5 ml) contained 50 µl of the tritiated ligand, (either the 5-$HT_4$ antagonist [$^3H$]GR113808, or the agonist [$^3H$]5-HT), 0.4 ml of membrane preparation (at 0.012 mg/ml of protein for [$^3H$]GR113808 binding or 0.1 mg/ml for [$^3H$]5-HT), and 50 µl solvent for total binding, or 50 µl of 10 mM SB204070 to determine non specific binding. The [$^3H$]GR113808 assay buffer was 50 mM HEPES/NaOH pH 7.5. The [$^3H$]5-HT assay buffer was Tris-HCl pH 7.4 containing 10 mM $MgCl_2$, 1 mM pargyline (monoamine oxidase inhibitor) and 1 mM paroxetine (5-HT transport inhibitor). The mixture was incubated 1 hour at 25° C. The incubation was terminated by rapid filtration over Whatman GF/B filters presoaked in 0.15% polyethylenimine and three washing steps with 3 ml of 50 mM HEPES/NaOH pH 7.5 for [$^3H$]GR113808 binding, presoaked and three washing steps with 3 ml Tris-HCl pH 7.4 for [$^3H$]5-HT binding. Ligand concentration isotherms were obtained using 8 concentrations of [$^3H$]GR113808 form 20 pM to 0.8 nM, and for [$^3H$]5-HT either 8 concentrations from 0.2 nM to 6 nM or from 0.2 nM to 40 nM were chosen. Competition binding experiments were performed with 0.25 nM of [$^3H$]GR113808 and otherwise at the same conditions as for [$^3H$]GR113808 saturation binding. Ligand concentration binding isotherms (rectangular hyperbola) and sigmoidal inhibition curves were calculated by nonlinear regression analysis according to algorithms described by Oestreicher and Pinto (1987). The maximal number of binding sites ($B_{max}$) and equilibrium dissociation constant ($K_D$) of the radioligand and the $pIC_{50}$ (negative logarithm of the concentration that inhibits 50% of specific binding by the radioligand) values of competitors were derived from the curve fitting. Apparent inhibition constant (Ki) values were calculated according to the equation of Cheng and Prusoff (1973). Graphs were prepared using the GraphPad Prism program.

Measurement of cAMP Formation

These experiments were done using the NEN adenylyl cyclase activation flashplate assay, according to the supplier. Cells were removed from the Petri dishes with 3 ml EDTA (0.04% w/v) and resuspended with phosphate buffered saline without $Ca^{2+}$ and $Mg^{2+}$. The cells were centrifuged at 1500 g for 5 minutes and the supernatants were removed. The pellet was resuspend in stimulation buffer and diluted to a concentration of $10^6$ cells/ml, 50 µl thereof were added per well of the flashplate (50000 cells/well). Compounds were diluted in PBS containing 1 mM pargyline and 1 mM paroxetine, and 50 µl of the resulting mixture was added per well, followed by an incubation for 20 minutes at 370° C. The final concentration of DMSO (whenever needed to dissolve the compounds) did not exceed 0.5% (vol/vol) and was also included in the corresponding control samples. The experiment was stopped and a direct $cAMP[^{125}I]$ detection assay was performed by adding 100 µl of detection mix per well. After incubation for 24 h at room temperature, counting was done in a Topcount (Packard).

Results

Cloning of the Human 5-$HT_{4(h)}$ Splice Variant

In the course of cloning the canine 5-$HT_4$ receptor cDNA by degenerate primer PCR based on our human 5-$HT_{4(b)}$ sequence (Van den Wyngaert et al., 1997) we found a variant (FIG. 1), similar to the partial porcine 5-$HT_{4(h)}$ cDNA originally designated 5-$HT_4B$ (published by Ullmer et al., 1995). In order to amplify this sequence also from human cDNA, we applied primers based on the d 5-$HT_{4(h)}$ specific sequence to different human cDNAs. However we succeeded only in amplifying the 5' part of a putative human homologue and did not receive PCR products for the 3' part of the ORF. In order to investigate, whether there is an extensive sequence diversity between the human and canine version of this exon, respectively whether this exon exists at all in human, we screened a human genomic DNA BAC library for a clone containing the human 5-$HT_4$ gene. One positive clone, 228K23 (Research Genetics) was identified. DNA prepared from this clone was sequenced using primer FW B2 (5'AACCAAGGCCTGGGCCAGGATTTTC ATGGG3', SEQ ID NO:13), complementary to a part of the 5-$HT_{4(h)}$ exon. The resulting sequence stretched into the adjacent intron sequence, design of a reverse primer complementary to that intron sequence allowed complete sequence determination of the human 5-$HT_{4(h)}$ exon sequence. Based on this information, h-variant specific forward and reverse primers were designed and combined with primer FW ONstart and reverse primers specific for the a and b splice variant. However for the latter, only the b variant specific primer REV 3non produced a PCR product of expected size in combination with FW B1. The two PCR products were fused by using the unique StyI restriction enzyme site in the nucleotide sequence of the 5-$HT_{4(h)}$ specific exon to build a full length reading frame.

Tissue Distribution of the 5-$HT_{(4h)}$ mRNA

Figure 2:
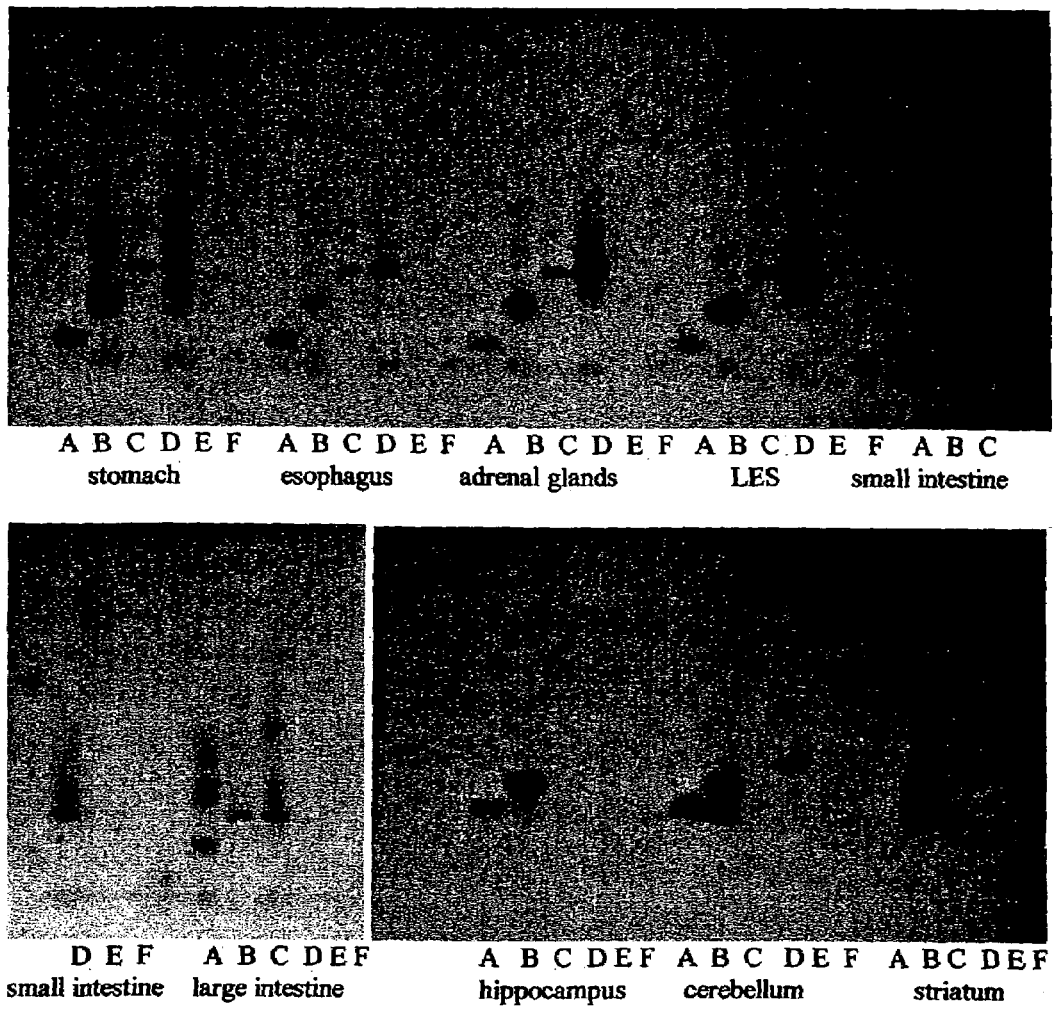
FIG. 2: is an illustration of mRNA tissue distribution performed as described in Materials and Methods. The letters indicate the used primer combination in the PCR, A:FW AB1/REV B1 (5' part 5-$HT_4$ cDNA including h exon), B:FW AB1/REV AB2 (common part of all 5-$HT_4$ splice variants), C:FW AB2/REV SH1 (3' part 5-$HT_{4a}$ cDNA), D:FW AB2/REV LO1 (3' part 5-$HT_{4b}$ cDNA), E:FW B1/REV SH1 (3' part 5-$HT_4$ cDNA, combination of exon h and a), F:FWB1/REV LO1 (3' part 5-$HT_{4(h)}$).

In an initial experiment to explore the specific function of the 5-$HT_{4(h)}$ in human physiology, we performed a tissue distribution study. The primers were chosen in order to obtain PCR products from parts of the 5-$HT_4$ cDNA that are common to all different variants and also to obtain bands that are specific for the a, b or h exon (FIG. 2). The only tissue from which detectable levels of a PCR product corresponding to the 5-$HT_{4(h)}$ variant, could be produced, was the lower esophageal sphincter (LES). For a number of the examined tissues, we found PCR products corresponding to the presence of h exon mRNA, but not in combination with the a or b specific C-terminal exon, in these cases, the h specific exon may be fused to another C-terminal exon of the 5-$HT_4$ gene. All other examined tissues showed bands corresponding to either the a or b splice variant, but not to the h variant.

Figure 3:
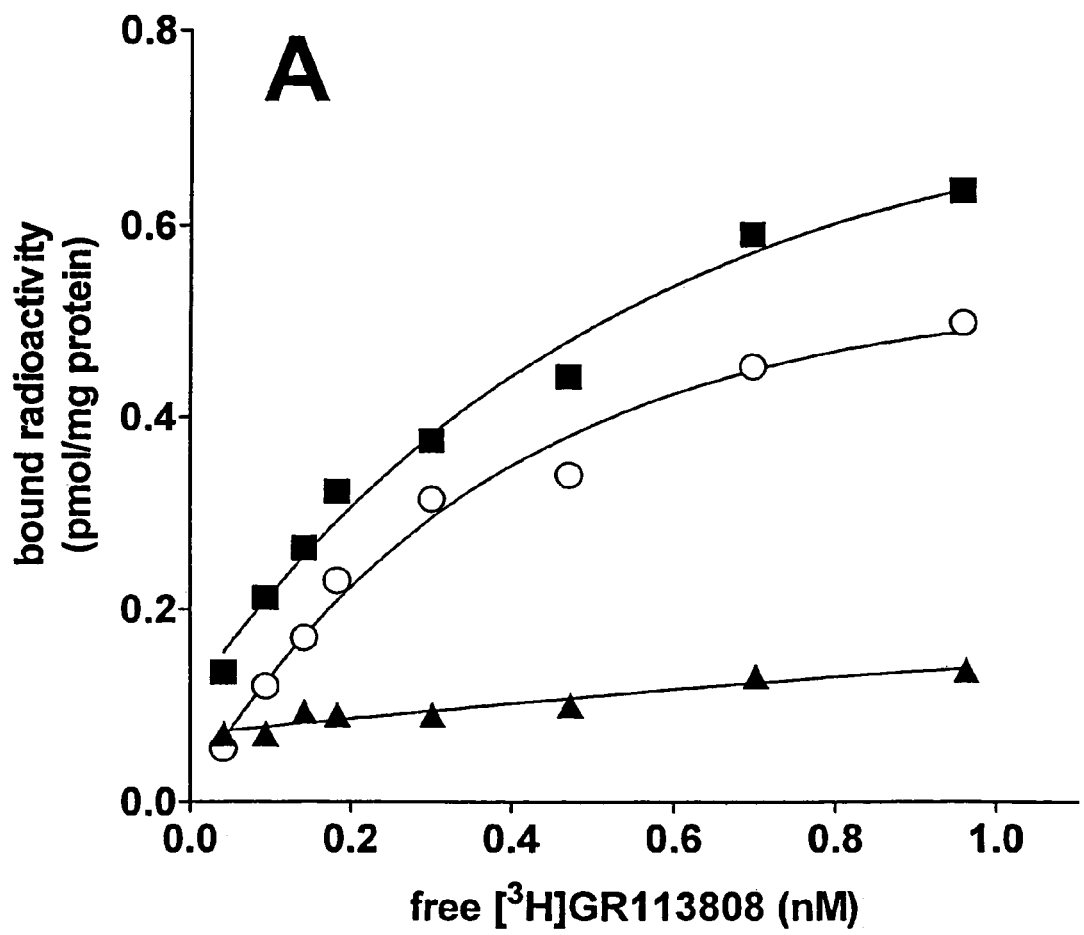
FIG. 3: Saturation analysis of [$^3$H]GR113808 binding on membrane preparation from COS-7 cells transfected with the h 5-$HT_{4(h)}$.

Transient Expression of the 5-$HT_{4(h)}$ Variant in Mammalian Cells and Pharmacological Characterization In order to compare the pharmacological properties of the 5-$HT_{4(h)}$ variant with those of the previously cloned 5-$HT_{4(a)}$ and b variant, the three corresponding pcDNA3 expression constructs were transiently transfected into COS cells. The receptors were investigated by radioligand binding assays on membrane preparations. Saturation analysis experiments were performed with the agonist [$^3$H]5-HT as well as with the antagonist [$^3$H]GR113808. Antagonist and agonist saturation binding of the h variant from 3 independent transfections resulted in a straight line in Scatchard analysis, revealing a single high-affinity binding site. The ligand concentration isotherms of the h 5-$HT_{4(h)}$ revealed a $K_D$ of 0.24 (+/−0.17) nM using the antagonistic ligand and 1.65 (+/−0.55) nM based on the agonistic ligand (FIGS. 3A and B).

Figure 4:
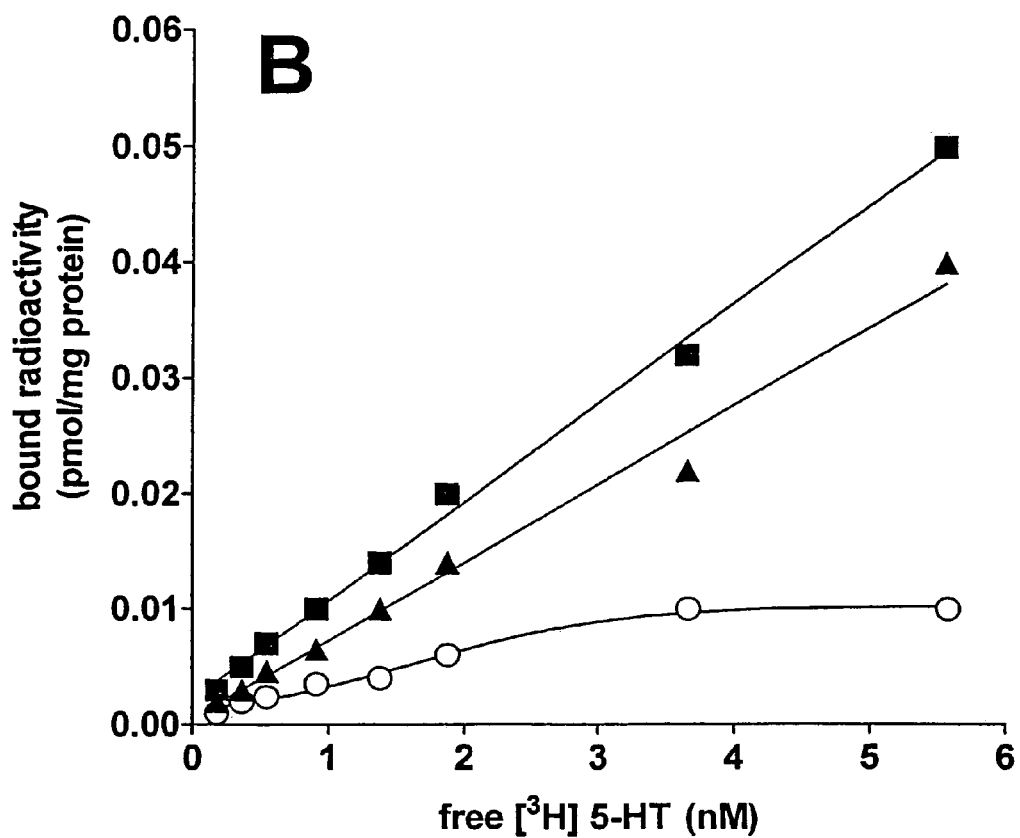
FIG. 4: Saturation analysis of [$^3$H]5-HT binding on membrane preparation from COS-7 cells transfected with the h 5-$HT_{4(h)}$.
Figure 5:
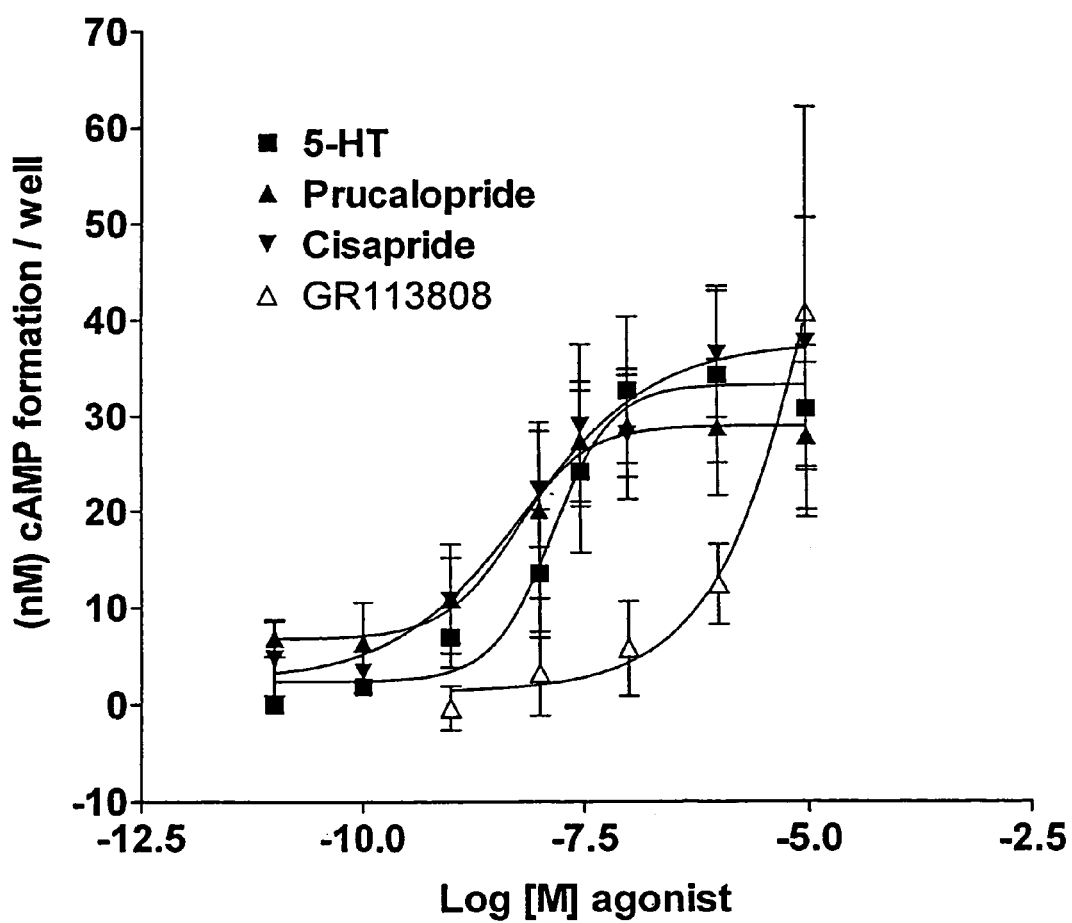
FIG. 5: Inhibition of specific [$^3$H]GR113808 binding by 5-HT$_4$ agonist and antagonist. Membrane preparations from COS-7 cells transiently transfected with h 5-HT$_{4(h)}$ receptor were incubated with 0.25 nM [$^3$H]GR113808. Non-specific binding was determined by 10 mM SB204070. Results are percentages, 100% is defined by specific binding in the absence of competing compound. Results are the mean of three independent experiments from three different transfections. Calculated pIC50 values are given in Table 1.
Figure 6:
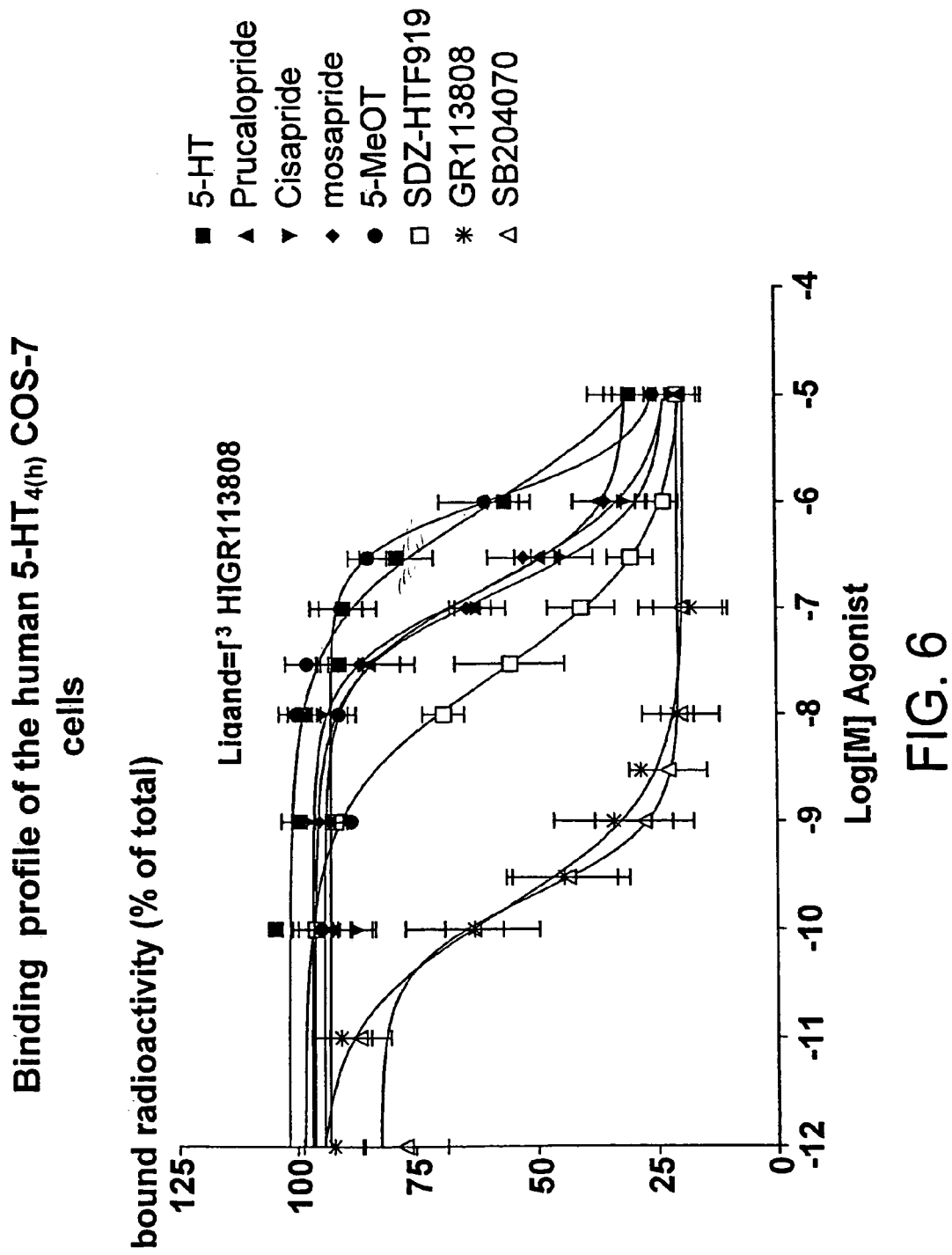
FIG. 6: Indirect estimation of AC stimulation by measuring cAMP formation in COS-7 cells transiently transfected with h 5-HT$_{4(h)}$. Results represent the increase of cAMP after stimulation by agonist since basal level has been removed. Results are the mean of three independent experiments from three different transfections. Calculated pEC50 and % of 5-HT$_{max}$ values are given in Table 2. The efficacy and potency of the different agonists to trigger the cellular response was estimated and compared for the three different variants. The mean of pEC50 and the percentage of stimulation, normalized for the maximum stimulation induced by 5-HT (% of 5-HT maximum) for the h5-HT$_{4(h)}$, h5-HT$_{4(a)}$ and h 5-HT$_{4(b)}$, are presented in Table 2. No difference in the pEC50 was noticed. The cAMP assay has been performed also for COS-7 cells transfected with the empty vector as a negative control. After stimulation with 10$^{-6}$ M of each agonist, 5-HT, cisapride and prucalopride, no significant increase of the cAMP basal level was found.

These values were not significantly different from the two other variants we investigated as reference, the $K_D$ of the variants a and b were respectively 0.14 (+/−0.06) and 0.19 (+/−0.07) nM for [$^3$H]GR113808 saturation binding and 3.7 (+/−0.6) and 4.6 (+/−1.9) nM for [$^3$H]5-HT saturation binding. The h 5-$HT_{4(h)}$ receptor displayed a Bmax of 605 (+/−174) fmol/mg of protein with [$^3$H]GR113808, and 61 (+/−12) fmol/mg of protein with [$^3$H]5-HT. Scatchard analysis from [$^3$H]5-HT binding suggested two affinity sites for the two 5-$HT_4$ receptor variants a and b. For each of the 3 independent transfections, COS-7 cells transfected with the vector alone showed no specific binding using the radioligand [$^3$H]GR113808. Saturation binding experiments with [$^3$H]GR113808 and [$^3$H]5-HT were performed in parallel for each of the 3 independent transfections. The resulting ratio of the Bmax found using the antagonistic radioligand versus the Bmax based on the agonistic radioligand reveals the proportion of the coupled receptors among the total number of receptors. We found this proportion to be 9.8 (+/−1.05) for the h5-$HT_{4(h)}$. The same result was obtained for the Bmax values found for the high affinity sites of the 2 reference 5-HT receptor variants a and b. However using the Bmax values obtained with the low affinity site, yielded a ratio of coupled receptors to total receptors that was 3 times lower. This result suggests a difference in the G-protein coupling of the h 5-$HT_{4(h)}$ variant, compared to the h 5-$HT_{4(a)}$ and h 5-$HT_{4(b)}$ variant. The pharmacological binding profile of the h5-$HT_{4(h)}$ was studied by competition binding assays using six different agonists and two antagonists in combination with the radioligand [$^3$H]GR113808 at a concentration of 0.25 nM (FIG. 4) on COS-7 membranes. Results are the mean of three independent transfections.

The 5-HT$_4$ receptor is suggested to be involved in a number of different physiological processes, which makes it an important pharmacological target. 5-HT$_4$ receptor activation influences gastrointestinal motility (Meulemans and Schuurkes, 1992), bladder function (Candura et al., 1996), exerts chronotropic and inotropic effects at the heart (Kaumann et al., 1990) and centrally enhances striatal dopamine release (Bonhomme et al., 1995) as well as associative memory in rats (Marchetti-Gauthier et al., 1997). This variety of physiological effects is paralleled by a variety of splice variants which have been discovered in the course of the last two years (Gerald et al., 1995; Claeysen et al., 1996; Van den Wyngaert et al., 1997; Claeysen et al., 1997; Blondel et al., 1997; Blondel et al., 1998). For these splice variants up to now no well documented specific biochemical or physiological properties described. However for splice variants of other GPCRs more information is available. For the C-terminal splice variants of the prostaglandin EP$_3$ receptor coupling to different G-proteins and signal transduction systems has been shown (Namba et al., 1993). C-terminal splice variants of the mouse somatostatin receptor differ in the efficiency of adenylate cyclase inhibition and receptor desensitization (Vanetti et al., 1993). Differential splicing at the third intracytoplasmic loop of the PACAP receptor leads to coupling to different G- proteins (Spengler et al., 1993), the same was found for C-terminal splice variants of mGluR1 (Pin et al. 1992). Pickering et al. (1993) showed for the same variants in addition differential intracellular distribution. For some of these GPCR splice variants also differential tissue distribution has been shown (Spengler et al., 1993), also this is not the case for others (Pin et al., 1992). The up to now published 5-HT$_4$ splice variants all vary in their C-terminus, which suggests in analogy to the results obtained from other GPCRs that they may differ from each other in respect to G-protein usage, desensitization and/or subcellular localization. The 5-HT$_{4(h)}$ variant described in this study has an extra insertion of 14 amino acids in the second extracellular loop, to our knowledge there are no other descriptions of such a variation produced by alternative splicing. Surprisingly this modification led to the loss of the low affinity agonist binding site that was found for the a and b splice variant. Although the ratio of coupled to uncoupled receptor is still the same for the high affinity agonist binding site across all three known variants, it is likely that the insertion of 14 amino acids into the second extracellular loop leads to a change of receptor topology that is reflected in G-protein binding. This change in receptor topology is also suggested by the agonistic effect that GR113808 exerts at this variant, which acts as an antagonist at all other 5-HT$_4$ variants. The availability of a variety of 5-HT$_4$ splice variants offers the opportunity for medicinal chemistry to pursue a higher degree of specificity for drug development. Given that the standard 5-HT4 receptor antagonist GR 113 808 showed agonistic activity on the 5-HT4(h) receptor variant and that 5-HT4 receptor antagonists are under investigation as compounds for the treatment of irritable bowel syndrome (IBS), testing of any given ligand on the 5-HT4(h) variant is essential before classifying it as an 5-HT4 receptor antagonist. Based on the specific tissue distribution of the 5-HT$_{4(h)}$ to the LES, compounds showing specificity towards that 5-HT$_4$ splice variant may have therapeutic value for the treatment of heartburn, reflux, irritable bowel syndrome, esophagitis, Barrett=s esophagus, esophageal cancer, achalasia, esophageal stenosis, esophagel spasms, esophageal hiatal hernia or other esophageal motility disorders. Furthermore these compounds may be of value in the treatment of airway disorders possibly connected with oesophageal irritation, such as asthma, bronchospasms, aspiration and its consequences (bronchitis, (broncho)pneumonia, bronchiectasia).

Compounds acting on 5-HT$_4$ receptor splice variants found in the lower oesophageal sphincter, may additionally be useful in treating or alleviating the symptoms of diseases of the lower oesophageal sphincter or other conditions such as achalasia; oesophageal stenosis (due to systemic sclerosis, tumours, burns) or compression, oesophageal spasms or other oesophageal motility disorders, irritable bowel syndrome, asthma, bronchospasms and other airway disorders possibly connected with oesophageal irritation aspiration and its consequence (bronchitis, (broncho)pneumonia, bronchiectasia, . . . ); (hiatus) hernia; denervation of the oesophagus (e.g. after certain types of trauma or surgery), disturbances in oesophageal innervation; pregnancy (not a disease or even a condition that as such could be treated with 5HT4-receptor compounds, but one in which—for various reasons-oesophageal reflux and its consequences are more common); emesis; postoperative ileus; diabetic gastroparesis.

Abbreviations used: AC, adenylyl cyclase; DMEM, Dulbecco's modified Eagle medium; DMSO, dimethyl sulfoxide; 5-HT, 5-hydroxytryptamine, serotonin; Ki, inhibition constant; LES, lower esophagael sphincter; ORF, open reading frame.

REFERENCES

Blondel, O., Vandecasteele, G., Gastineau, M., Leclerc, S., Dahmoune, Y., and Fischmeister, R. (1997) Molecular and functional characterization of a 5-HT$_4$ receptor cloned from human atrium. *FEBS Letters* 412, 465–474.

Blondel, O., Gastineau, M., Dahmoune, Y., Langlois, M., and Fischmeister, R. (1998) Cloning, expression, and pharmacology of four human 5 hydroxytryptamine$_4$ receptor isoforms produced by alternative splicing in the carboxyl terminus. *J. of Neurochemistry* 70, 2252–2261.

Bonhomme, N., De Deurwaerdere, P., Le Moal, M., and Spampinato, U. (1995) Evidence for 5-HT4 receptor subtype invovment in the enhancement of striatal dopamine release induced by serotonin: a microdialysis study in the halothane-anesthetized rat. *Neuropharmacology* 34 (3), 269–279.

Buchheit, K.-H. and Buhl, T. (1991) Prokinetic benzamides stimulate peristaltic activity in the isolated guinea pig ileum by activation of 5-HT$_4$ receptors. *Eur. J. Pharmacol.* 205, 203–208.

Candura, S. M., Messori, E., Franceschetti, G. P., D=Agostino, G., Vicini, D., Tagliani M., and Tonini M. (1996) Neural 5-HT4 receptors in the human isolated detrusor muscle: effects of indole, benzimidazolone and substituted benzamide agonists and antagonists. *Br. J. Pharmacol.* 118, 1965–1970.

Claeysen, S., Sebben, M., Laurent, J., Bockaert, J., and Dumuis, A. (1996) Cloning, expression and pharmacology of the mouse 5-HT4L receptor. *FEBS Letters* 398, 19–25.

Claeysen, S., Faye, P., Sebben, M., Lemaire, S., Bockaert, J., and Dumuis, A. (1997) Cloning and expression of human 5-HT4S receptors. Effect of receptor density on their coupling to adenylyl cyclase. *NeuroReport* 8, 3189–3196.

Dumuis, A., Bouhelal, R., Sebben, M., Cory, R., and Bockaert, J. (1988) A non-classical 5-hydroxytryptamine receptor positively coupled with adenylate cyclase in the central nervous system. *Mol. Pharmacol.* 34, 880–887.

Eglen, R. M., Wong, E. H. F., Dumuis, A., and Bockaert, J. (1995) Central 5-HT$_4$ receptors. *Trends in Pharmacol. Sci.* 16, 391-398.

Elswood, C. J., Bunce, K. T., and Humphrey, P. P. A. (1991) Identification of putative 5-HT4 receptors in guinea-pig ascending colon. *Eur. J. Pharmacology* 196, 149–155.

Fontana D. J., Daniels, S. E., Wong, E. H., Clark, R. D. and Eglen, R. M. (1997) The effects of novel 5-hydroxytryptamine (5-HT)$_4$ receptor ligands in rat spatial navigation. *Neuropharmacology* 36 (4), 689–696.

Galeotti, N., Ghelardini, C., and Bautolini, A. (1998) Role of 5-HT4 receptors in the mouse passive avoidance test. *J. Pharmacol. & Exp. Therapeutics* 286 (3), 1115–1121.

Gerald, C., Adham, N., Kao, H.-T., Olson, M. A., Laz, T. M., Schechter, L. E., Bard, J. A., Vaysse, J.-J., Hartig P. R., Branchek, T. A., and Weinshank, R. L. (1995) The 5-HT4 receptor: molecular cloning and pharmacological characterization of two splice variants. *EMBO J.* 14 (12), 2806–2815.

Hedge, S. S. and Eglen, R. M. (1996) Peripheral 5-HT4 receptors. *FASEB J.*, 10 (12), 1398–1407.

Kaumann, A. J., Sanders, L., Brown, A. M., Murray, K. J. and Brown, M. J. (1990) A 5-hydroxytryptamine receptor in human atrium. *Br. J. Pharmacol.* 100, 879–885.

Lefevbre, H., Contesse, V., Delarue, C., Fevilloley, M., Hery, F., Grise, P., Raynaud, G., Verhofstad, A. A. J., Wolfe, L. M. and Vaudry, H. (1992) *Neuroscience* 47, 999

Maniatis, T., Fritsch, E. F., and Sambrook, J. (1982) *Molecular Cloning: A Laboratory Manual.* Cold Spring Harbor, N.Y.

Marchetti-Gauthier, E., Roman, F. S., Dumuis, A., Bockaert, J., and Soumireu-Mourat, B. (1997) BIMU1 increases associative memory in rats by activating 5-HT4 receptors. *Neuropharmacology* 36 (4/5), 697–706.

Meulemans, A. L. and Schuurkes, A. J. (1992) Is the action of cisapride on the guinea pig ileum mediated via 5-HT4 receptors. *Eur. J. of Pharmacol.* 212, 51–59.

Monferini, E., Gaetani, P., Baena, R. R., Giraldo, E., Parenti, M., Zocchetti, A., and Rizzi, C. A. (1993) Pharmacological characterization of the 5-Hydroxytryptamine receptor coupled to adenylyl cyclase stimulation in human brain. *Life Sciences* 52, 61–65.

Moummi, C., Yang, D.-C., and Gullikson, G. W. (1992) 5-HT4 receptor relaxation and associated cAMP generation in rat esophagus. *Eur* 47–52.

Namba, T., Sugimoto, Y., Negishi, M., Irie, A., Ushikubi, F., Kakiz Ichikawa, A., and Narumiya, S. (1993) Alternative splicing of C prostaglandin E receptor subtype EP3 determines G-protein speci 166–170.

Pickering, D. S., Thomsen, C., Suzdak, P. D., Fletcher, E. J., Robitai M. W., MacDonald, J. F., Huang, X.-P., and Hampson, D. R. (1993) A alternatively spliced forms of a metabotropic glutamate receptors phosphoinositide turnover. *J. of Neurochemistry* 61, 85–92.

Pin, J.-P., Waeber, C., Prezeau, L., Bockaert, J., and Heinemann, S Alternative splicing generates metabotropic glutamate receptors patterns of calcium release in Xenopus oocytes. *Proc. Natl. Aca* 10331–10335.

Silvestre, J. S., Fernandez, A. J., and Palacios, J. M. (1996) Effects antagonists on rat behaviour in the elevated plus—maze test. 309 (3), 219–222.

Spengler, D., Waeber, C., Pantaloni, C., Holsboer, F., Bockaert, J. Journot, L. (1993) Differential signal transduction by five spl PACAP receptor. *Nature* 365, 170–175.

Ullmer, C., Schmuck, K., Kalkman, H. O., AND Lübbert, H. (1995) Expr receptor mRNAs in blood vessels. *FEBS Letters* 370, 215–221.

Van den Wyngaert, I., Gommeren, W., Verhasselt, P., Jurzak, M., Ley and Bender, E. (1997) Cloning and expression of a human seroton cDNA. *J. of Neurochemistry* 69, 1810–1819.

Vanetti, M., Vogt, G., and Höllt, V. (1993) The two isoforms of the receptor (mSSTR2A and mSSTR2B) differ in coupling efficiency to and in agonist-induced receptor desensitization. *FEBS Letters* 3.

Vilaro, M. T., Cortes, R., Gerald, C., Branchek, T. A., Palacios, J. M (1996) Localization of 5-HT4 receptor mRNA in rat brain by in s histochemistry. *Mol. Brain Res.* 43, 356–360.

TABLE 1

Comparison of potency of compounds to compete with 0.25 nM [$^3$H]GR113808 binding in membranes from COS-7 cells transiently transfected with respectively human 5-HT$_{4(h)}$, 5-HT$_{4(a)}$ or 5-HT$_{4(b)}$ receptors.

| Compounds | Human 5-HT4 h receptor in Cos-7 cells pIC50 +/– SD (n) pKi | Human 5-HT4 a receptor in Cos-7 cells pIC50 +/– SD (n) pKi | Human 5-HT4 b receptor in Cos-7 cells pIC50 +/– SD (n) pKi |
|---|---|---|---|
| Agonist | | | |
| 5HT | 6.09 +/– 0.05 (3) 6.43 | 6.80 +/– 0.37 (3) 6.89 | 6.47 +/– 0.18 (3) 6.63 |
| Prucalopride | 6.74 +/– 0.24 (3) 8.03 | 7.20 +/– 0.40 (4) 7.21 | 7.04 +/– 0.25 (4) 7.16 |
| Cisapride | 6.78 +/– 0.32 (3) 7.05 | 7.22 +/– 0.47 (4) 7.23 | 6.92 +/– 0.33 (4) 6.99 |
| Mosapride | 6.55 +/– 0.24 (3) 6.85 | 6.48 +/– 0.19 (3) 6.71 | 6.04 +/– 0.27 (3) 6.18 |
| SDZ-HTF919 | 7.45 +/– 0.52 (3) 7.59 | 8.08 +/– 0.66 (4) 7.86 | 7.89 +/– 0.20 (4) 8.09 |
| 5-MeOT | 5.82 +/– 0.27 (3) 6.1 | 6.09 +/– 0.53 (4) 6.08 | 6.11 +/– 0.52 (4) 6.13 |
| Antagonist | | | |
| SB204070 | 10.01 +/– 0.17 (3) 10.38 | 10.07 +/– 0.32 (4) 10.15 | 9.98 +/– 0.16 (4) 10.04 |
| GR113808 | 9.05 +/– 0.31 (3) 9.29 | 9.45 +/– 0.35 (4) 9.54 | 9.39 +/– 0.13 (4) 9.57 |

TABLE 2

Comparison of potency and affinity of agonist compounds to stimulate cAMP formation in COS-7 cells transiently transfected with respectively human 5-HT$_{4(h)}$, 5-HT$_{4(a)}$, or 5-HT$_{4(b)}$ receptors.

| | % of 5HT max (+/− SD) | | | pEC50 (+/1 SD) | | |
|---|---|---|---|---|---|---|
| | 5-HT4 variants | | | | | |
| | a | b | h | a | b | h |
| Compounds | n = 5 | n = 8 | n = 3 | n = 5 | n = 8 | n = 3 |
| 5HT | 100 | 100 | 100 | 8.24 (+/−0.156) | 8.31 (+/−0.147) | 7.9 (+/−0.26) |
| Prucalopride | 118 (+/−7.2) | 117.36 (+/−3.4) | 95 (+/−11.6) | 8.24 (+/−0.105) | 8.49 (+/−0.049) | 8.36 (+/−0.62) |
| Cisapride | 98.17 (+/−7.5) | 113.62 (+/−4.36) | 123.53 (+/−20.85) | 7.82 (+/−0.26) | 7.9 (+/−0.113) | 7.99 (+/−0.62) |
| GR113808 | 0 | 0 | 54.6 (+/−5.8) | — | — | 7.95 (+/−0.38) |

The invention claimed is:

1. An isolated nucleic acid molecule encoding the amino acid sequence of SEQ ID NO: 2.

2. The nucleic acid molecule according to claim 1 which is a DNA molecule.

3. The nucleic acid molecule of claim 2, wherein said DNA molecule is a cDNA molecule.

4. A DNA expression vector comprising a nucleic acid molecule of claim 1.

5. A host cell transformed or transfected with the vector of claim 4.

6. The host cell according to claim 5, which cell is mammalian cell.

7. The host cell according to claim 6, which mammalian cell is a COS-7 cell.

8. A HEK 293 or COS-7 5-HT$_{4(h)}$ cell line transfected with the expression vector of claim 4.

9. A method of determining whether a compound is an agonist or an antagonist of a ligand of a human 5-HT$_{4(h)}$ receptor, which method comprises contacting a cell transformed or transfected with an expression vector according to claim 4 capable of expressing said receptor with said compound in the presence of said ligand and monitoring cAMP formation in said cell, wherein a change in cAMP formation in the cell identifies the compound as an agonist or an antagonist.

10. The method of claim 9 wherein said cell is a human cell.

11. A method of determining whether a compound binds to a human 5-HT$_{4(h)}$ receptor which method comprises contacting a cell, or a membrane preparation from the cell wherein the cell was transformed or transfected with an expression vector according to claim 4 capable of expressing said receptor, with said compound and determining the binding affinity of said compound for said receptor.

12. A kit for determining whether a compound is an agonist or an antagonist of a 5-HT$_{4(h)}$ ligand, which kit comprises a cell according to claim 4, means for contacting said compound and said ligand with said cell and means for measuring cAMP formation Is said cell.

13. A kit according to claim 12 wherein said cell Is a COS-7 cell.

14. An isolated receptor protein comprising the amino acid sequence of SEQ ID NO:2.

* * * * *